US008312160B2

(12) United States Patent
Van Meerbergen et al.

(10) Patent No.: US 8,312,160 B2
(45) Date of Patent: Nov. 13, 2012

(54) WIRELESS SENSOR NODE ARCHITECTURE WITH AUTONOMOUS STREAMING

(75) Inventors: Jozef Louis Van Meerbergen, Zoersel (BE); Anteneh Alemu Abbo, Eindhoven (NL); Martinus Theodorus Bennebroek, Den Bosch (NL); Octavio Santana, Eindhoven (NL); Lennart Yseboodt, Hove (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 127 days.

(21) Appl. No.: 12/863,809

(22) PCT Filed: Jan. 26, 2009

(86) PCT No.: PCT/IB2009/050296
§ 371 (c)(1),
(2), (4) Date: Jul. 21, 2010

(87) PCT Pub. No.: WO2009/095834
PCT Pub. Date: Aug. 6, 2009

(65) Prior Publication Data
US 2010/0293288 A1    Nov. 18, 2010

(30) Foreign Application Priority Data
Jan. 28, 2008    (EP) .................................... 08150716

(51) Int. Cl.
*G06F 15/16*    (2006.01)
(52) U.S. Cl. ...................................... 709/230; 709/231

(58) Field of Classification Search .................. 709/230, 709/231
See application file for complete search history.

(56) References Cited

OTHER PUBLICATIONS

Lettieri et al: "A QoS-Aware, Energy-Efficient Wireless Node Architecture"; 1999 IEEE International Workshop on Mobile Multimedia Communications (MOMUC'99), Nov. 1999, pp. 252-261.
Branson et al: "Clasp: Collaborating, Autonomous Stream Processing Systems"; Middleware 2007, Lecture Notes in Computer Science (LNCS), Nov. 2007, vol. 4834, pp. 348-367.
Handziski et al: "Flexible Hardware Abstraction for Wireless Sensor Networks"; IEEE Proceedings of the Second European Workshop on Wireless Sensor Networks, 2005, pp. 145-157.
"Part 15.4: Wireless Medium Access Control (MAC) and Physical Layer (PHY) Specifications for Low-Rate Wireless Personal Area Networks (WPANs)"; IEEE Standard for Information Technology, 2006, pp. 1-26.
Ye et al:"An Energy-Efficient MAC Protocol for Wireless Sensor Networks"; USC/Information Sciences Institute, Proceedings of the IEEE INFOCOM, Jun. 2002, pp. 1567-1576.
Calhoun et al: "Design Considerations for Ultra-Low Energy Wireless Microsensor Nodes"; IEEE Transactions on Computers, Jun. 2005, vol. 54, No. 6, pp. 727-740.

*Primary Examiner* — Adnan Mirza

(57) ABSTRACT

A sensor device includes at least one autonomous streaming module. Predetermined internal events of the autonomous streaming module or predetermined external events from streaming data at an interface to a smart shell of the autonomous streaming module are detected. An operational mode of a component or subsystem within the smart shell of the autonomous streaming module is controlled in response to the detection.

16 Claims, 9 Drawing Sheets

WIRELESS SENSOR NODE ARCHITECTURE WITH AUTONOMOUS STREAMING

FIELD OF THE INVENTION

The present invention relates to a sensor device and method for collecting sensor data in sensor networks, such as—but not limited to—body sensor networks.

BACKGROUND OF THE INVENTION

The benefits of collecting medical information from a person over a long time period and during everyday life have long been prophesized. In recent years, many research groups have been investigating body sensor networks (BSNs). These are networks of multiple sensors or sensing devices or sensing nodes, deployed around, and even in, the body and transmitting their data over a digital radio link. Thus, each sensor should be as discrete and small as possible.

A number of protocols are currently known which purport to be protocols for 'low-power' networks and might therefore be suitable for BSNs. Examples of such protocols are described in "Part 15.4: Wireless Medium Access Control (MAC) and Physical Layer (PHY) Specifications for Low-Rate Wireless Personal Area Networks (LR-WPANs)", IEEE Std 802.15.4-2006, and Wei Ye et al. "S-MAC: An Energy-Efficient MAC Protocol for Wireless Sensor Networks". A BSN, by its very nature, is a mobile network and can be worn on or implanted in the body, for example. Additionally, an access device or 'collating' device may be provided, which collects data from the sensor nodes and which may also be worn on the body.

Power consumption is an important issue in most wireless sensor network applications. For instance, in personal health monitoring, the wearable and implanted sensor nodes are equipped with very small batteries and are required to be functional for a long duration. Although the application characters might differ in the way the sensor nodes are operated, a common requirement is an energy-efficient mode of operation. Since the sensor node architecture has a big impact on the power consumption, proper choice needs to be made to satisfy the stringent requirements. Another requirement is reliability. If the nodes are used in biomedical monitoring they need to operate reliably, even with unpredictable hardware behavior.

Recently a number of wireless sensor nodes are made available on the market to cater for the growing needs of the emerging applications. Aside from innovations regarding the components (e.g., processors, radio, analog-to-digital converter (A/D)), most wireless sensor nodes are composed in a traditional way in which a control processing unit (CPU) or direct memory access (DMA) device takes care of data transfer to and from the peripherals. As an example, B. Calhoun, et al, "Design Considerations for Ultra-low Energy Wireless Microsensor nodes", IEEE Trans. on Computers, Vol. 54, No. 6, June 2005 describes a DMA based sensor node built from modules with independent voltage and frequency islands to improve the overall energy efficiency. An event which is generated when a buffer is full is used to trigger operation of the associated module. Although the use of DMA is more energy efficient than a CPU in moving data, there are a number of drawbacks associated with both approaches.

First, lack of predictability arises from the fact that the CPU and the DMA device are shared devices that operate on an interrupt basis which makes them intrinsically non-predictable in the sense that service requests could be missed. Such lack of predictability could even lead to non-real time response to critical events which for real-time alert applications is not acceptable. In the proposed invention, any unpredictability in data transfer is removed, making the whole system more robust.

Second, a transfer overhead is generated from the point of view of data transport between components, a CPU or DMA device with its accompanying operation protocol introduces an overhead that essentially reduces energy efficiency.

Third, lack of hardware scalability arises from the fact that the DMA device is a central shared resource which is not easily scalable when a sensor node needs to change operational mode with distinctly different performance requirements and/or handles multiple data streams originating from multiple sensor units, primarily due to the limited number of DMA channels.

Fourth, programming complexity results from the fact that from application programmer point of view, (re-)configuring the DMA device and/or peripherals is not a simple task and could lead to non-optimal operation modes. Moreover, switching-off components when temporarily not needed can be extremely favorable for energy efficiency. Unfortunately, this often requires a significant programming effort (and, therefore, is sometimes even just completely ignored) as waking-up components is non-trivial due to the intrinsic wake-up times (related to e.g. power-up and/or stabilization) that somehow need to be accounted for in the application program.

SUMMARY OF THE INVENTION

An object of the present invention is to provide an improved sensor architecture and sensing method, which alleviate or prevent the mentioned drawbacks by exploiting the characteristics of the data flow between the components in wireless sensor nodes.

Accordingly, an "autonomous" data transfer mechanism can be provided, which avoids the use of a CPU or DMA device and therefore offers minimum power consumption. Moreover, an autonomous wake-up and/or sleep-down mechanism can be implemented, where the CPU is not involved at all and, thereby, programming complexity is relieved as well. By introducing autonomous streaming modules that will have a simple and uniform programmer interface (e.g. open, close, read, write, input/output control), software (driver) portability is facilitated and automatic system generation is possible. The proposed system architecture which is based on autonomous streaming modules thus provides an energy-efficient wireless sensor node integration. The autonomous streaming modules can be built from subsystems or components that are encapsulated in the smart-shells which detect pre-specified internal events or events from the streaming data and control the activity of the subsystem or component. The streaming paradigm allows the subsystems to communicate with each other with the lowest possible overhead, thereby improving the system-level power efficiency. In addition to this, the proposed solution enhances system-level performance predictability, reduces programming complexity and exhibits better hardware scalability.

The control unit may be adapted to control the operational mode of the component or subsystem based on internal events generated by a timer, so that time-dependent control of the operation mode or operation state of the subsystem or component is possible.

Furthermore, a shared control bus for configuring and monitoring said component or subsystem, and connection-based streaming channels for transferring data between components or subsystems of the at least one autonomous streaming module can be provided. Thereby, streaming communication can be separated from control signaling.

The smart shell may comprise the control unit, a stream communication port adapted to generate said external events based on stream content, and a local manager adapted to interpret the generated external events. This modular and autonomous topology enables energy-efficient operation of the sensor node. In a specific example, the local manager may comprise an operation controller for controlling the operation mode based on at least one of detected events and status of said component or subsystem.

Additionally, a streaming communication subsystem may be provided in one of the at least one autonomous streaming modules, the streaming communication subsystem comprising a switch network and a connection scheduler adapted to control the switch network to provide connections based on a control information supplied to the connection scheduler. Thereby, streaming connections can be pre-configured by the control and status bus.

The control unit of the sensor node may comprise at least one communication port for providing a communication link to the component or subsystem.

Furthermore, a stream interface module may be provided, which comprises an input register at a streaming channel side, an output register at a side of the subsystem or component, and an event detector for signaling an event based on the content of at least one of the input and output registers. Thus, an event signal can be generated based on the streaming data in the input and output registers.

The at least one control unit may be adapted to select the operation mode from an active mode, a standby mode, and a sleep mode. Operation mode setting may be achieved for example by controlling power and clock supply of the component or subsystem.

Further advantageous embodiments are defined below.

BRIEF DESCRIPTION OF THE DRAWINGS

The invention will now be described, by way of example, based on an embodiment with reference to the accompanying drawings, wherein.

DETAILED DESCRIPTION OF AN EMBODIMENT

Various embodiments of the present invention will now be described based on a BSN system as an example of a wireless sensor network.

Figure 1:
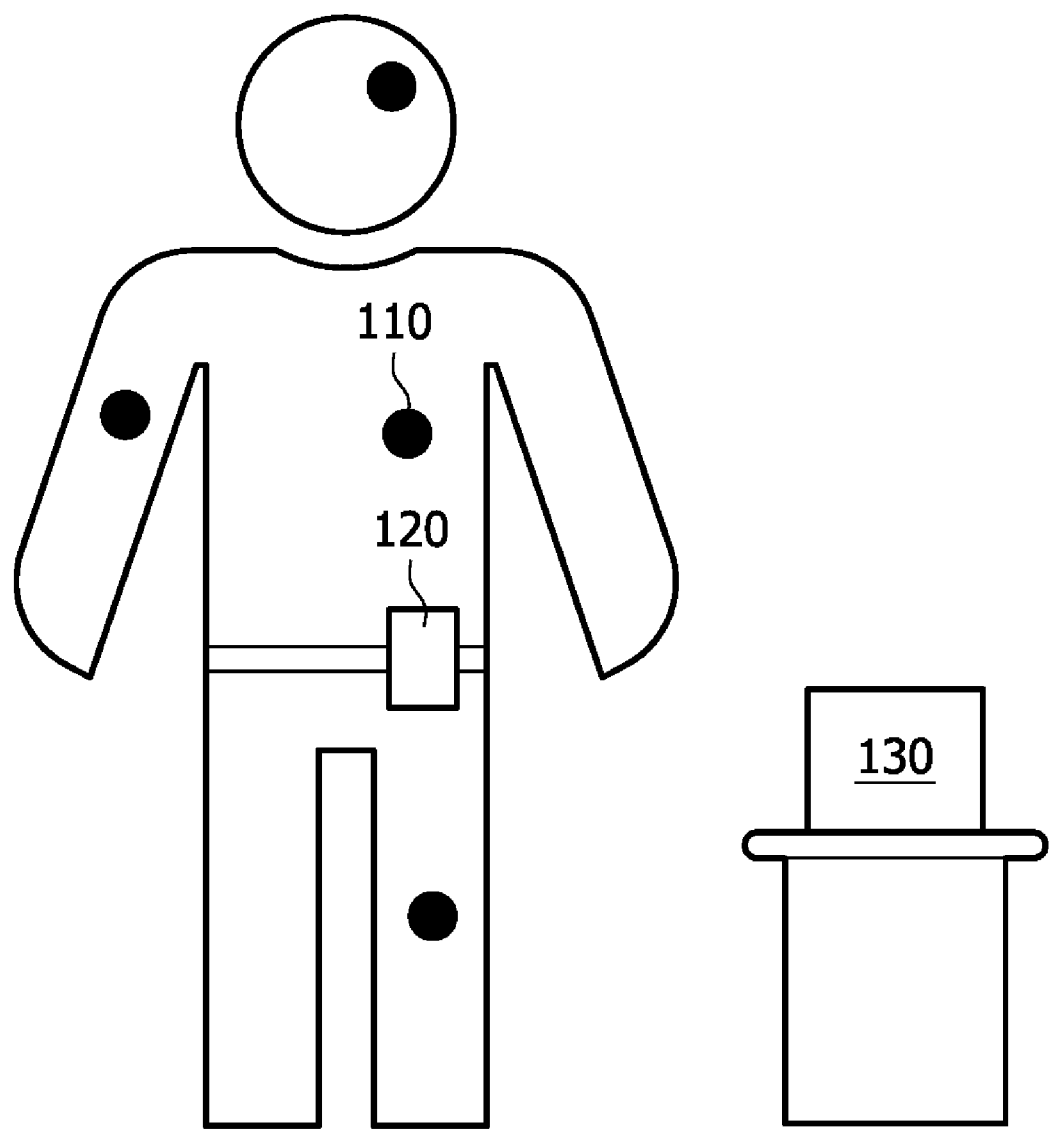
FIG. 1 shows a schematic human body with a sensor network and collating devices.

FIG. 1 shows a schematic diagram of a BSN system with a number of locations on a body, where sensor nodes or devices 110 are attached. Besides the sensor nodes 110 located around or implanted in the body, the BSN system may comprises one or more access or collating devices 120, 130, which receive signals or sensing data from the sensor nodes 110 and which may be configured to upload the received information to a central server (not shown).

In the exemplary arrangement of FIG. 1, a mobile access or collating device 120 is configured to be worn somewhere on the body (e.g. on a belt), and/or may alternatively be integrated into an electronic device, such as a mobile phone, which would be carried anyway. Additionally, a fixed access or collating device 130 may be located in specific areas (e.g. at home, for example in the lounge and bedroom), which can be powered from the mains and which is configured to collect data whilst the user is located in the vicinity thereof.

Different types of sensors may be provided in the sensor nodes 110. E.g., a sensor for sensing a temperature of a body region where it is attached to. A person may wear one or more of these—to measure the temperature on/in the body both on the torso and at the extremities. Additionally, a sensor may be provided for sensing oxygen saturation of the blood, which is usually measured through the skin by detecting the 'redness' of the blood. Another type of sensor may be worn to detect the movement and level of activity of the wearer. Research has shown that this can also allow the current activity (sitting, walking, running etc.) to be inferred. Another sensor may be provided to measures an electrical signal generated as the heart beats, by reading the differential voltage at the skin across the heart. Still other sensor may detect a rate of breathing and coughs, a number of steps taken (pedometer), a blood pressure, either using traditional 'cuff' mechanism, or by using timing information between a heartbeat and arrival of the pulse at an extremity.

According to the embodiment, a system architecture is provided, which is based on autonomous streaming modules (ASMs) for energy-efficient wireless sensor node (WSN) integration. The ASMs are built from components or subsystems that are encapsulated in smart-shells which detect pre-specified events from streaming data and control the activity or operation mode of the sub-system. Each smart shell controls the operational mode of the allocated component of subsystem. This control is provided by a control manager that monitors "data" events at smart shell interfaces and/or internally-generated events by e.g. a local timer or the like. Configuration status monitoring of the smart shell and its embedded component is arranged through a control (or configuration) block. Typical examples of components are digital sensor interfaces, interfaces to analog-to-digital (A/D) and digital-to-analog (D/A) converters, memory cores, processor cores, and transceiver blocks.

Figure 2:
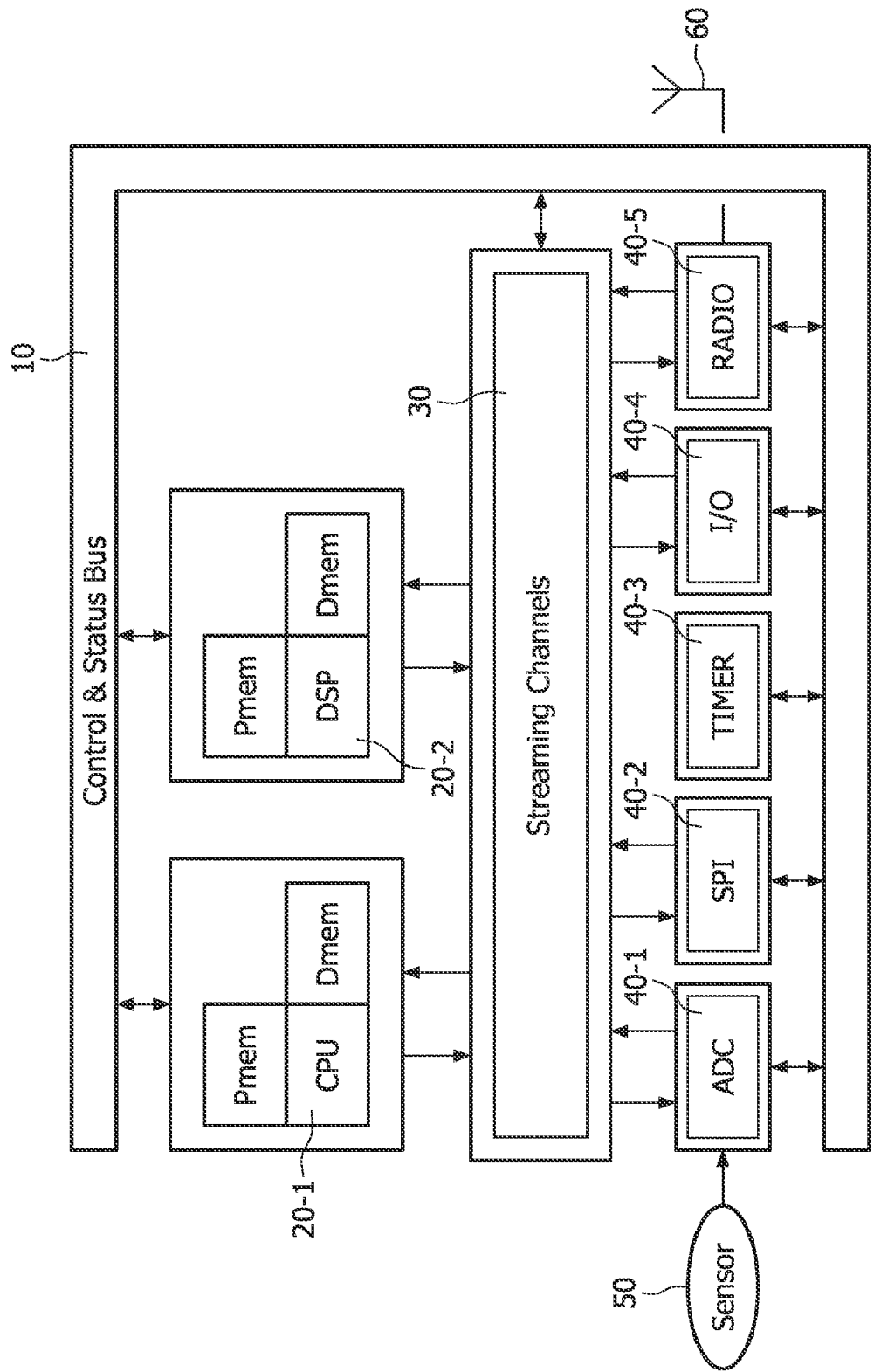
FIG. 2 shows a schematic block diagram of a wireless sensor architecture according to an embodiment.

FIG. 2 shows a schematic block diagram of an embodiment of the proposed wireless sensor node architecture. The system includes a central processing unit (CPU) 20-1 for managing the system operation, a digital signal processor (DSP) 20-2 for handling computing intensive tasks and a number of peripherals, e.g. ADC 40-1, system packet interface (SPI) 40-2, timer 40-3, input/output (I/O) interface 40-4, radio unit 40-5, for interfacing with the outside world. The radio unit 40-5 provides connection to a radio antenna 60, where radio signals generated in the radio unit 40-5 can be emitted. The above peripherals, the CPU 20-1 and the DSP 20-2 can be connected via streaming channels 30 for data exchange, and are controlled via a control and status bus (or bus system) 10.

Thus, autonomous subsystems are built by "wrapping" the subsystems or components with smart shells. Each smart shell can be regarded as a circuitry which provides a smart or intelligent interface between the wrapped or enclosed subsystem and component and the outer circuitry, e.g., control and status bus 10 and streaming channels 30. Thereby, a clear separation of communication channels can be achieved, wherein a tightly-coupled local communication is provided within the components or subsystems (e.g., program and data memory accesses in the subsystems of CPU 20-1 and DSP 20-2). Furthermore, the shared control and status bus 10 is provided for configuring and monitoring the components or subsystems, and the connection-based streaming channels 30 are provided for transferring data between the components or subsystems. Thereby, hardware event can be handled for guaranteed and low-overhead data transfer.

FIGS. 3A to 3D show exemplary information flows in the wireless sensor architecture of FIG. 2, to indicate how the components or subsystems interact in the proposed sensor node architecture.

Figure 3A:
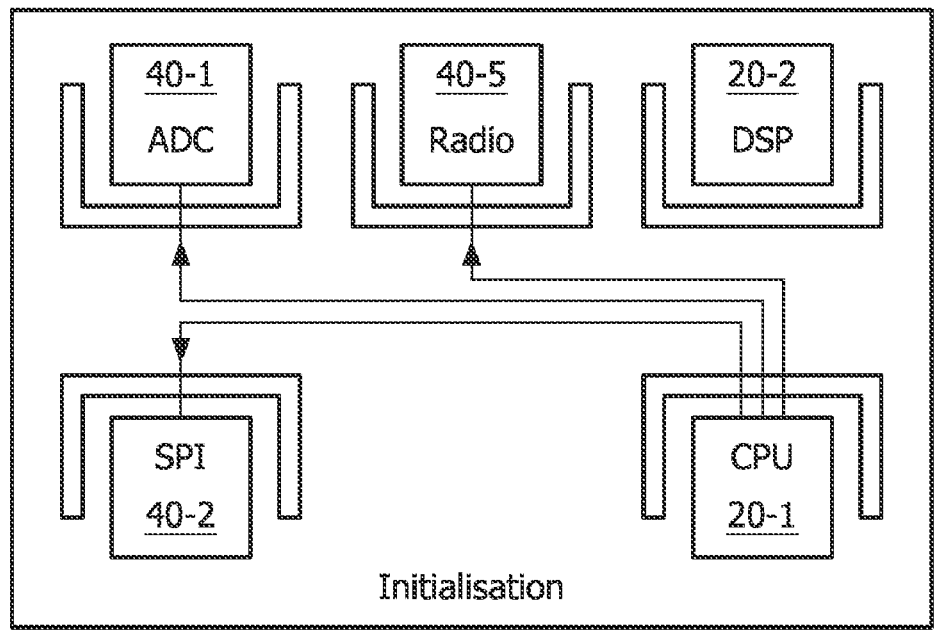
FIGS. 3A to 3D show exemplary information flows in the wireless sensor architecture according to the embodiment.

In FIG. 3A, the CPU 20-1 initializes the system up by configuring the shells. In this example, the ADC 40-1 is configured to deliver samples to the DSP 20-2 at a certain rate. Likewise, the radio unit 40-5 and the SPI interface 40-2 are configured to accept outgoing data streams.

Figure 3B:
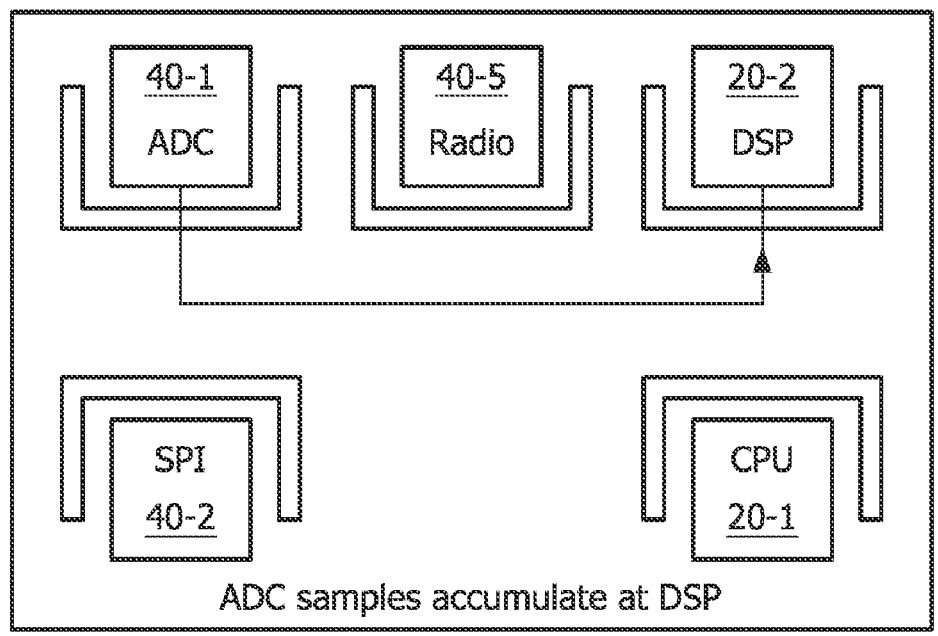

In FIG. 3B, initialization is complete and the ADC 40-1 starts to stream input samples that are accumulated in the shell of the DSP 20-2.

Figure 3C:
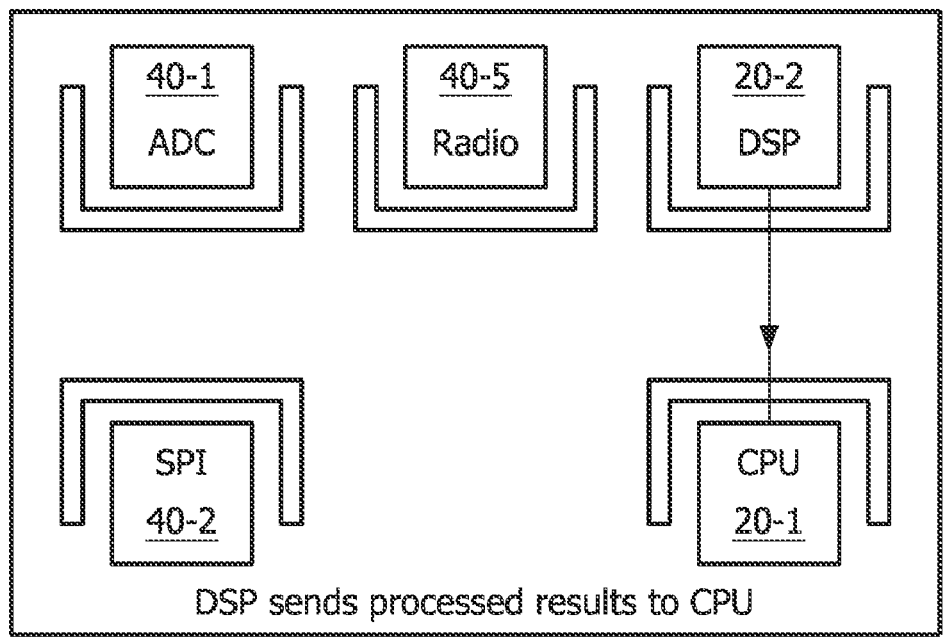

In FIG. 3C, a pre-defined number of samples has been reached and the shell of the DSP 20-2 wakes up the DSP 20-2 which will then process the collected samples and stream out the result to the shell of the CPU 20-1. The CPU shell wakes up the CPU 20-1 when an event is detected, e.g. when a certain number of samples has been received from the DSP 20-2. Based on the result of the DSP analysis, the CPU 20-1 decides what to do.

Figure 3D:
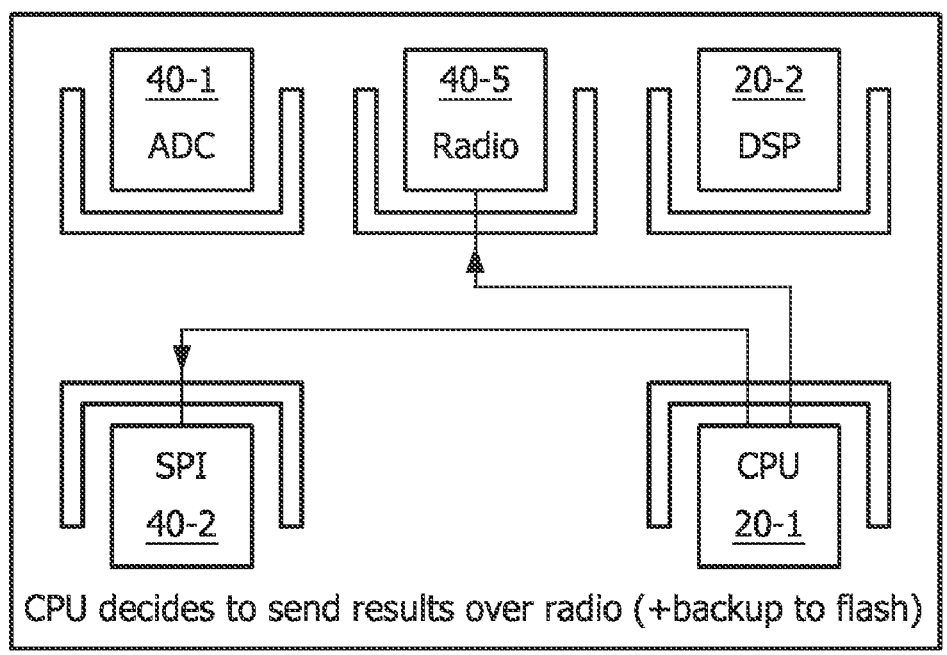

In this case, as shown in FIG. 3D, it sends a message over the radio unit 40-5 and keeps a backup copy stored in flash via the SPI interface 40-2.

Figure 4:
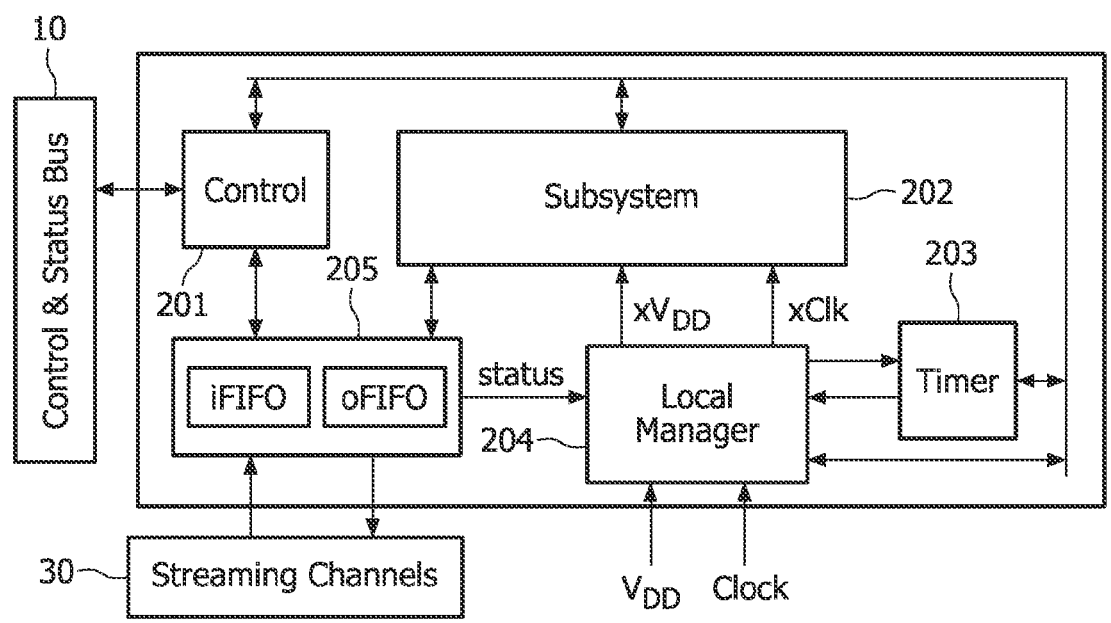
FIG. 4 shows a schematic block diagram of an autonomous subsystem architecture according to the embodiment.

FIG. 4 shows a schematic block diagram of an architectural embodiment of an autonomous sensor node subsystem. The smart shell is built from modules that enable energy-efficient operation of the subsystem 202. The smart shell or wrapper comprises a control unit 201 which is used by the CPU 20-1 to set configuration registers in the subsystem 202 or the wrapper and communicate status information. Furthermore, a stream communication port or stream interface module 205 built from FIFOs (first-in-first-out memories or serial shift registers) is capable of generating events based on the content of the stream. Additionally, a local manager 204 interprets the events from the stream interface module 205 and a timer 203 to control the operating voltage (x$V_{DD}$) and clock (xClk) based on corresponding inputs ($V_{DD}$, Clock). The timer 203 which may be optional generates regular events that might be needed by some subsystems (e.g. A/D converters 40-1, CPU 20-1, radio unit 40-5, . . . ).

Figure 5:
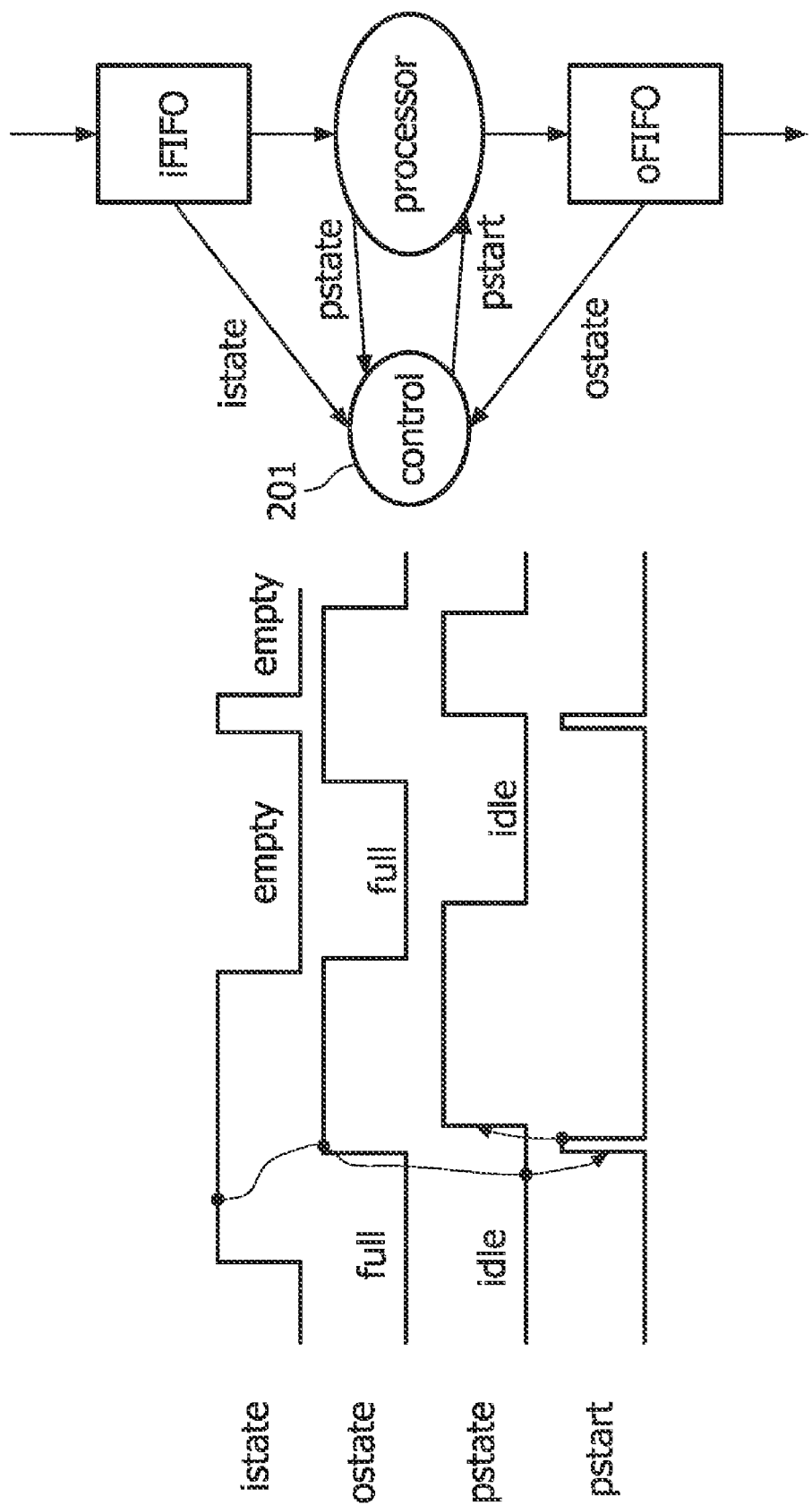
FIG. 5 shows a schematic signaling diagram of a streaming based data processing according to the embodiment.

FIG. 5 shoes a schematic signaling diagram of a streaming based data processing according to the embodiment, which is the basic principle of streaming based task execution. As indicated in the processing diagram on the right-hand side of FIG. 5, the control function of the control unit 201 checks events from the input and output FIFOs (istate and ostate) and the processor status (pstate) before issuing a command (pstart) to trigger start of an operation. Although in the timing diagram the signals istate and ostate are checked for empty and full conditions, respectively, a more flexible way would associate a pre-defined number of input data samples and output storage locations as events.

Figure 6:
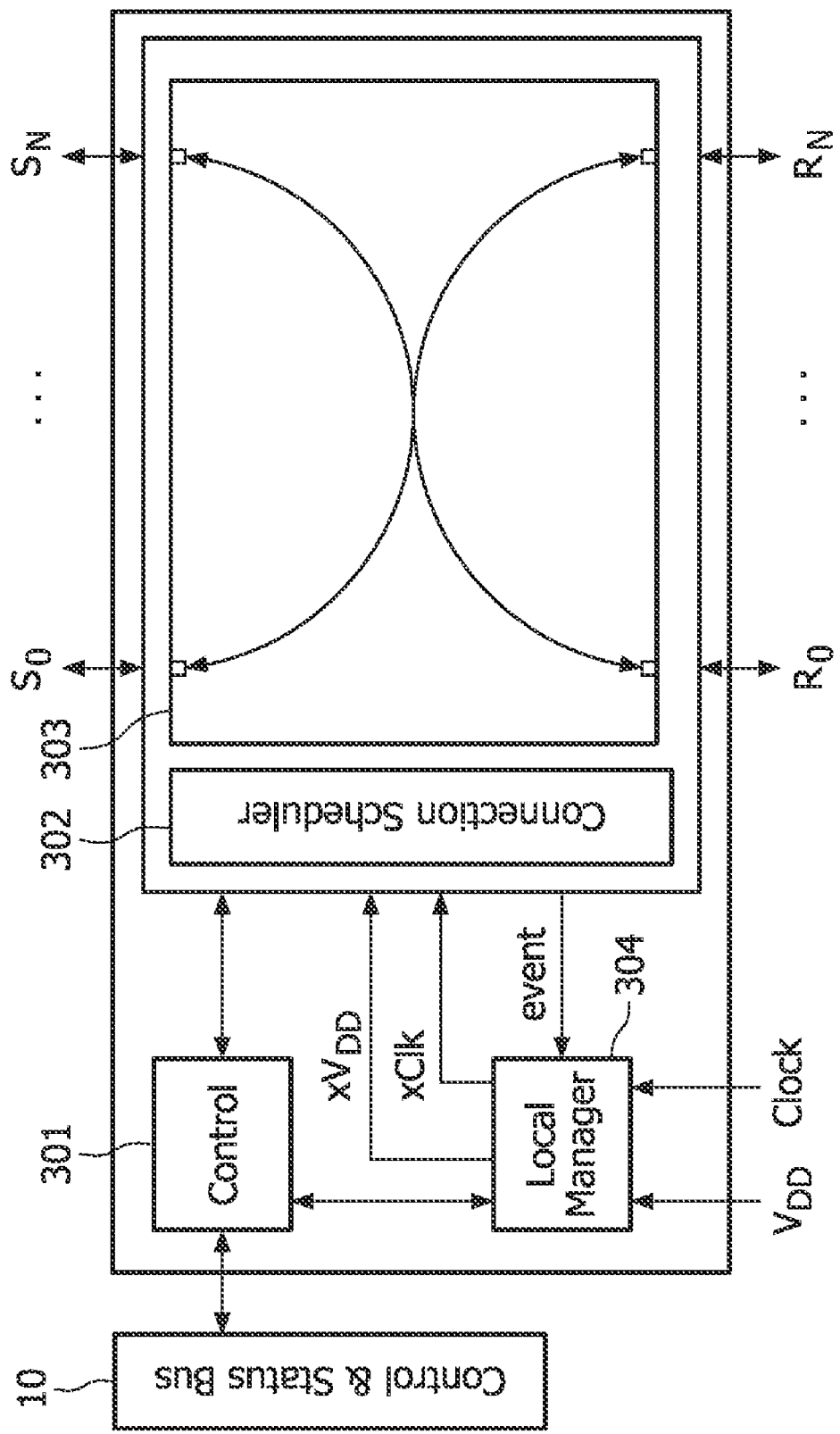
FIG. 6 shows a schematic block diagram of a streaming communication subsystem architecture according to the embodiment.

FIG. 6 shows a schematic block diagram of a streaming communication subsystem architecture according to the embodiment. A functionality of this subsystem is to establish a link between communicating devices, e.g. senders ($S_0$ to $S_N$) and receivers ($R_0$ to $R_N$). Which pairs of devices are linked depends on a control by a connection scheduler 302 which may be a digital circuit controlling switching states of a switch network 303 by which connections between the senders and receivers can be selectively connected. Connections are pre-configured by the CPU 20-1 via an interface to the control and status bus 10 and a control unit 301. Depending on the dynamics of the application, a local manager 304 in the shell or wrapper determines the best operating condition by controlling the supply voltage $V_{DD}$ and clock frequency Clock. Events from the streaming channels are used to trigger operations of the local manager 304.

Figure 7:
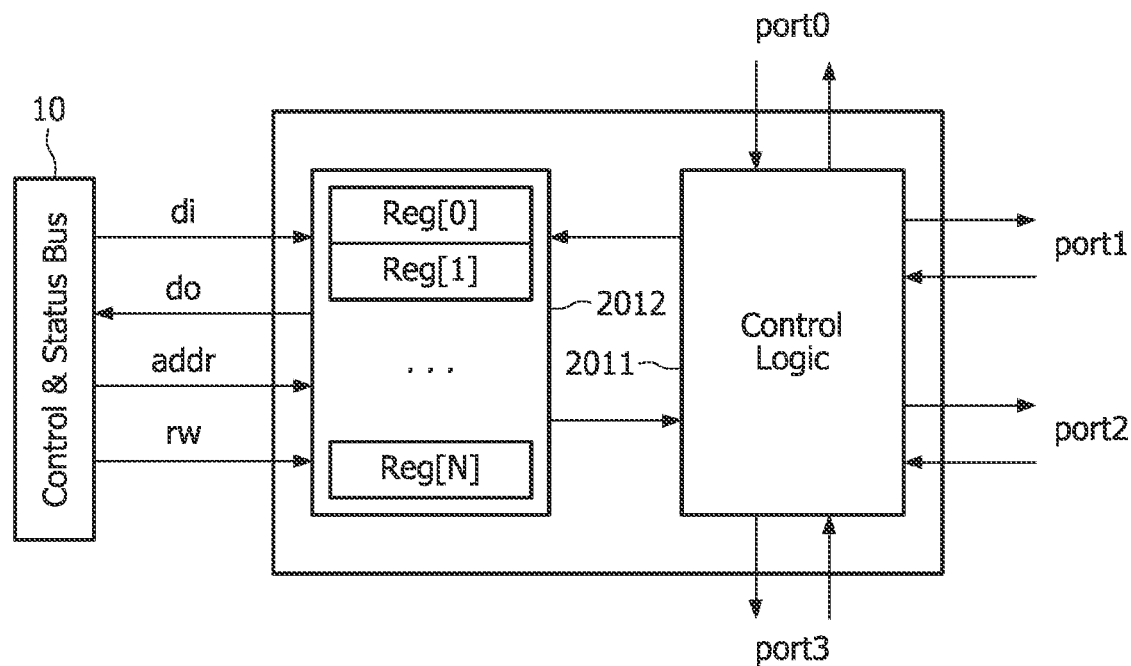
FIG. 7 shows a schematic block diagram of a subsystem controller architecture according to the embodiment.

FIG. 7 shows a schematic block diagram of a subsystem controller architecture, e.g. the control unit 201 of FIG. 4 or the control unit 301 of FIG. 6, in the smart shell, according to the embodiment. A register bank 2012 with registers Reg[0 . . . N] is used to store configuration data sent by the CPU 20-1 and status information generated by the subsystem 202. A control logic 2011 is responsible for interpreting the configuration data and taking actions that determine the mode of operation of the controlled subsystem 202, the stream interface module 205 and the local manager 204. As an example, four ports port0 to port3 are used to link the controller to the respective components.

Figure 8:
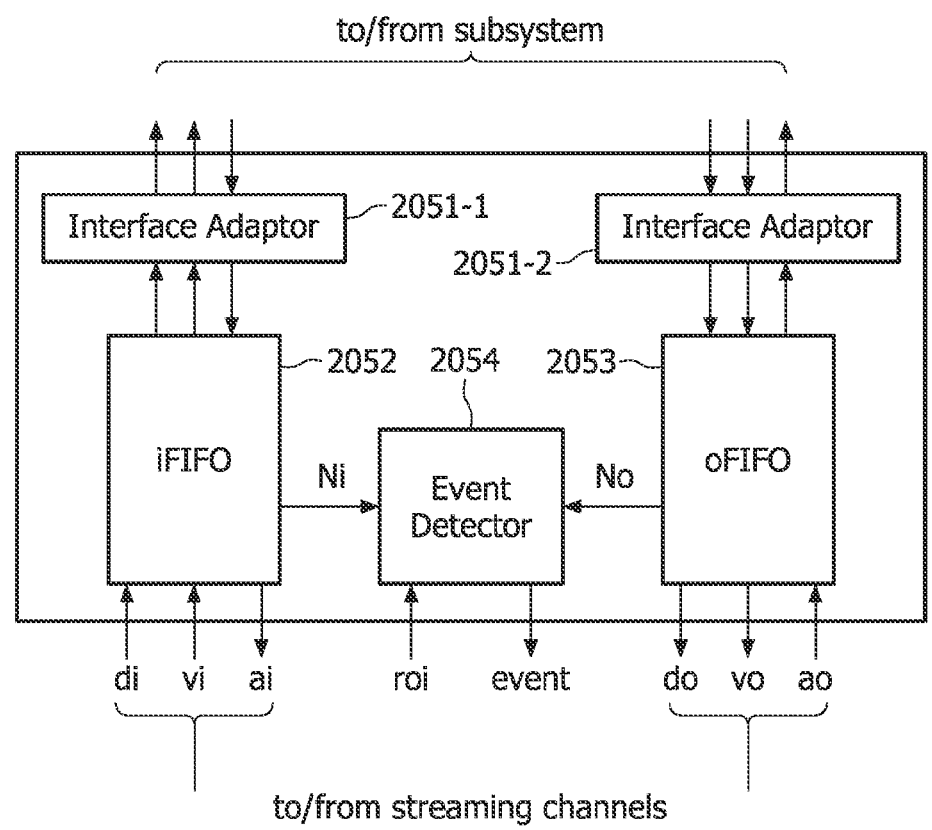
FIG. 8 shows a schematic block diagram of a stream interface module according to the embodiment.

FIG. 8 shows a schematic block diagram of the stream interface module 205 of FIG. 4. On the streaming channel side, an input FIFO 2052 and an output FIFO 2053 are connected via sdata (di, do), valid (vi, vo) and accept (ai, ao) signals. On the subsystem side, respective optional interface adaptors 2051-1 and 2051-2 are shown, which might be necessary when the subsystem interface protocol differs from that of the FIFOs 2052, 2053. An event detector 2054 generates an event signal event that is used by the local manager 204 based on input control signals Ni (number of iFIFO data elements), No (number of oFIFO data elements), and roi (ranges-of-interest).

Figure 9:
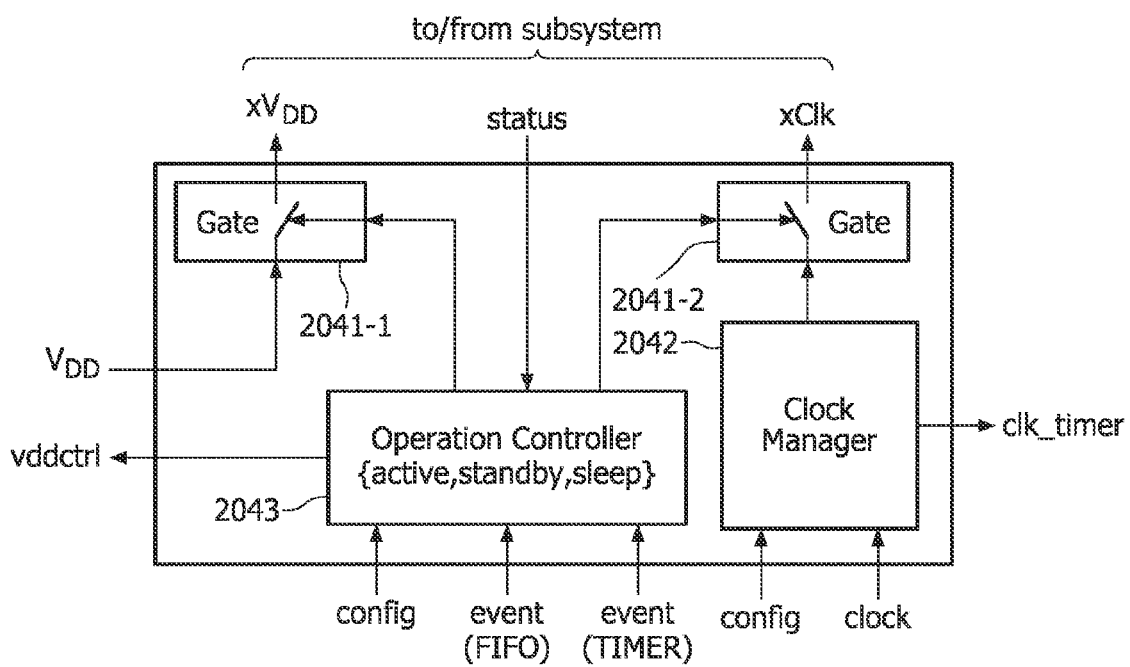
FIG. 9 shows a schematic block diagram of a stream interface module according to the embodiment.

FIG. 9 shows a schematic block diagram of a stream interface module which may be provided in the local manager 204 of FIG. 4. Based on events from the stream interface module 205 and/or the timer 203 and the status of the subsystem 202, an operation controller block 2043 decides the operation mode of the subsystem 202, e.g. an active, standby, or sleep mode. The power and clock gates are closed or opened by respective switching or gate circuits 2041-1 and 2041-2 based on the chosen mode of operation, e.g. active Mode (power gate x$V_{DD}$=ON and clock gate xClk=ON), standby mode (power gate x$V_{DD}$=ON and clock gate xClk=OFF) and sleep mode (power gate x$V_{DD}$=OFF and clock gate xClk=OFF).

Depending on the optimal operating condition of the subsystem 202, the supply voltage and the clock frequency could be dynamically adjusted. Voltage adaptation can be achieved by a control signal vddctrl that is sent to a voltage regulator (not shown). Furthermore, a configurable local clock manager 2042 is provided to generate appropriate clock(s) clk_timer to the subsystem 2042 and the shell components, based on configuration and clock inputs.

In summary, a sensor node and a method of controlling operation of the sensor node have been described, wherein the sensor node comprises at least one autonomous streaming module and wherein predetermined internal events of the autonomous streaming module or predetermined external events from streaming data at an interface to a smart shell of the autonomous streaming module are detected, and an operational mode of a component or subsystem within the smart shell of the autonomous streaming module is controlled in response to the detection.

The proposed architecture and processing can be applied in any kind of sensor systems where energy-efficiency needs to be combined with predictability. Thus, various applications from a growing field of wireless or non-wireless sensor networks can benefit from the proposed ideas. For example, in healthcare applications, remote (patient and/or elderly) monitoring services are of direct interest. For these applications, extremely reliable, easy-to-use, unobtrusive and low-cost wireless body sensor nodes are of great potential value when capable of continuously monitoring and logging patient conditions and, in case of anomalies, sending out real-time alert messages to nearby and/or remote service centers. Unlike existing WSN architectures, the proposed architecture offers an energy-efficient solution to many of the above requirements. Also for future in-body medical devices, where similar requirements exist though at much tighter dimensions (e.g. battery capacity), the proposed architecture can be of use. Alternatively, in lifestyle and lighting applications, various WSN applications are being under consideration that, in case of battery-powered nodes, can benefit from the proposed architecture.

The above embodiments can be implemented as well in body-coupled or body-based systems in many domains, or in other wireless or non-wireless sensor networks.

While the invention has been illustrated and described in detail in the drawings and the foregoing description, such illustration and description are to be considered illustrative or exemplary and not restrictive. The invention is not limited to the disclosed embodiments. From reading the present disclosure, other modifications will be apparent to persons skilled in the art. Such modifications may involve other features which are already known in the art and which may be used instead of or in addition to features already described herein.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. Although in the appended claims not all possible sub-combinations of claim features are claimed, it is intended to also include under the scope of protection of the claimed invention any combination of non-claimed sub-combinations of claim features. A single processor or other unit may fulfill the functions of blocks 201 to 205 of FIG. 4, blocks 301 to 304 of FIG. 6, blocks 2052 to 2054 of FIG. 8 and/or blocks 2042 and 2043 of FIG. 9, based on corresponding software routines. The computer program may be stored/distributed on a suitable medium, such as an optical storage medium or a solid-state medium supplied together with or as part of other hardware, but may also be distributed in other forms, such as via the Internet or other wired or wireless telecommunication systems. The mere fact that certain measures are recited in mutually different dependent claims does not indicate that a combination of these measures cannot be used to advantage. Any reference signs in the claims should not be construed as limiting the scope thereof.

The invention claimed is:

1. A sensor device for use in a sensor network, said sensor device comprising:
   a) a sensor which senses an external condition;
   b) at least one autonomous streaming module each having a subsystem encapsulated in a smart shell including:
      a stream communication port configured to generate external events based on a stream content, and
      a local manager configured to interpret said generated external events;
      at least one control unit configured for detecting predetermined internal events of said autonomous streaming module or predetermined external events from streaming data at an interface to said smart shell and for setting configuration registers for controlling an operational mode of said subsystem in response to the detected events;
   b) a shared control bus configured for configuring and monitoring said subsystem;
   c) connection-based streaming channels configured for transferring data between subsystems of said at least one autonomous streaming module, the streaming channels being connected with the stream communication port.

2. The sensor device according to claim 1, wherein said control unit is adapted to control said operational mode of said subsystem based on internal events generated by a timer.

3. The sensor device according to claim 1, wherein said local manager comprises an operation controller for controlling said operation mode based on at least one of detected events and status of said subsystem.

4. The sensor device according to claim 1, wherein a streaming communication subsystem is provided in one of said at least one autonomous streaming modules, said streaming communication subsystem comprising a switch network and a connection scheduler configured to control said switch network to provide connections based on a control information supplied to said connection scheduler.

5. The sensor device according to claim 1, wherein said control unit comprises at least one communication port configured for providing a communication link to said subsystem.

6. The sensor device according to claim 1, wherein the stream interface module includes an input register at a streaming channel side and an output register at a side of said subsystem, and an event detector configured for signaling an event based on the content of at least one of said input and output registers.

7. The sensor device according to claim 1, wherein said at least one control unit is configured to select said operation mode from an active mode, a standby mode, and a sleep mode.

8. The sensor device according to claim 1, wherein said at least one control unit is configured to set said operation mode by controlling power and clock supply of said subsystem.

9. A method of controlling operation of a sensor device or sensor node, said method comprising:
   with a sensor, sensing an external condition and generating analog sensor data;
   converting the analog sensor data to digital sensor data;
   streaming the digital sensor data on a plurality of streaming channels;
   generating events based on the streaming digital sensor data;
   configuring registers of a subsystem via a control bus different from the streaming channels with a control unit;
   interpreting the streaming digital sensor data; and
   controlling operating voltages and a clock of the subsystem in accordance with the interpreting of the streaming digital data.

10. A non-transitory computer readable medium comprising a set of instructions for controlling an apparatus to execute the steps according to claim 9.

11. A body sensor network comprising:
a plurality of sensor devices, said sensor devices comprising:
  a) a computer processing unit;
  b) at least one autonomous streaming module each having a subsystem encapsulated in a smart shell, the streaming module including a plurality of streaming channels;
  c at least one control unit controlled by the computer processing unit for detecting predetermined internal events of said autonomous streaming module or predetermined external events from streaming data at an interface to said smart shell and for controlling an operational mode of said subsystem in response to detected events,
  d) a timer, and
  e) a local manager configured to interpret the internal and external events;
at least one access device for data collection from said sensors devices;
a sensor which measures at least one of heart beats, body temperature, blood oxygen saturation, breathing rate, and blood pressure.

12. The sensor device according to claim 1, wherein the sensor measures at least one of heart beats, body temperature, blood oxygen saturation, breathing rate, and blood pressure.

13. The method according to claim 9, further including:
sensing physiological data of a patient with a sensor; and
digitizing the physiological data to generate the streaming digital sensor data.

14. A sensor node comprising:
a sensor which senses an external condition;
an analog-to-digital converter connected to the sensor to generate digital sensor data;
one or more digital signal processors including:
  a stream interface connected with the streaming channels for generating events based on streaming data on the streaming channels,
  a control unit controlled by the computer processing unit to set configuration registers in a subsystem, the control unit being connected with the control and status bus and the stream interface, the subsystem being connected with the control unit and the stream interface,
  a timer,
  a local manager which interprets the streaming data, the local manager being connected with the subsystem, the stream interface, and the timer to control operating voltages and a clock of the subsystem;
a computer processing unit for managing system operation;
a plurality of streaming channels interconnecting the analog-to-digital converter, the one or more digital signal processors, and the computer processing unit; and
a control and status bus, different from the streaming channels interconnecting the analog-to-digital converter, the one or more digital signal processors, and the computer processing unit.

15. The sensor node according to claim 14, further including:
a radio connected with the streaming channels, the control and status bus, and an antenna;
an input/output interface connected with the streaming channels, the control and status bus;
a timer connected with the streaming channels, the control and status bus; and
a system packet interface connected with the streaming channels, the control and status bus.

16. The sensor node according to claim 14, wherein the streaming channels have an architecture including:
a switch network by which connections are made between the analog-to-digital converter, the one or more signal processors, and the computer processing unit; and
a connection scheduler which controls switching states of the switching network;
a control unit controlled by the control and status bus;
a local manager which controls a supply voltage and a clock frequency for the connection scheduler.

* * * * *